United States Patent
Chen et al.

(10) Patent No.: US 9,061,989 B1
(45) Date of Patent: Jun. 23, 2015

(54) METHOD FOR PRODUCING TEREPHTHALIC ACID

(71) Applicant: FAR EASTERN NEW CENTURY CORPORATION, Taipei (TW)

(72) Inventors: Guei-San Chen, Taipei (TW); Fa-Chen Chi, Taipei (TW); Cheng-Han Chou, Taipei (TW); Xin-An Lu, Taipei (TW)

(73) Assignee: Far Eastern New Century Corporation, Taipei (TW)

( * ) Notice: Subject to any disclaimer, the term of this patent is extended or adjusted under 35 U.S.C. 154(b) by 0 days.

(21) Appl. No.: 14/489,262

(22) Filed: Sep. 17, 2014

(30) Foreign Application Priority Data

Mar. 21, 2014 (TW) .............................. 103110694 A

(51) Int. Cl.
*C07C 51/353* (2006.01)
*C07C 51/16* (2006.01)

(52) U.S. Cl.
CPC ............... *C07C 51/353* (2013.01); *C07C 51/16* (2013.01)

(58) Field of Classification Search
None
See application file for complete search history.

(56) References Cited

PUBLICATIONS

I. N. Nazarov et al. "Structural Orientation in the Diene Condensations of Isoprene with Unsymmetrical Dienophiles." *Russian Chemical Bulletin*. vol. 8, Issue 8. Aug. 1959: 1362-1369.
Takashi Inukai and Takeshi Kojima. "Catalytic Actions of Aluminum Chloride on the Isoprene-Methyl Acrylate Diels-Alder Reaction." *The Journal of Organic Chemistry*. vol. 31, Issue 4. Apr. 1966: 1121-1123.

*Primary Examiner* — Brian J Davis
(74) *Attorney, Agent, or Firm* — Ladas & Parry, LLP

(57) ABSTRACT

A method for producing terephthalic acid comprises the steps of: subjecting methyl acrylate to contact with aluminum chloride so as to form a complex; adding isoprene to the complex to result in a Diels-Alder reaction which is kept at a temperature no higher than 50° C. by cooling so as to obtain a cyclic adduct product; subjecting the cyclic adduct product to separation so as to obtain a cyclic para-precursor; and subjecting the cyclic para-precursor to a chemical reaction so as to obtain terephthalic acid.

12 Claims, No Drawings

METHOD FOR PRODUCING TEREPHTHALIC ACID

CROSS-REFERENCE TO RELATED APPLICATION

This application claims priority from Taiwanese Application No. 103110694, filed on Mar. 21, 2014, the entire disclosure of which is hereby incorporated in its entirety by reference.

BACKGROUND OF THE INVENTION

1. Field of the Invention

The invention relates to a method for producing terephthalic acid, more particularly to a method for producing terephthalic acid via a Diels-Alder reaction at a low temperature and in the absence of a solvent. The invention also relates to a method for producing methyl 4-methyl-3-cyclohexene-1-carboxylate, which is used for further producing terephthalic acid.

2. Description of the Related Art

Polyethylene terephthalate (hereinafter referred to as PET) is widely used in the industries for the manufacture of commodities, such as fibers, containers, and packaging materials, and purified terephthalic acid (hereinafter referred to as PTA) is one of the major monomer raw materials for PET.

Nazarov et al. (*Russ. Chem. Bull.* 1959, 8, 1362-1369) discloses a process for producing terephthalic acid by subjecting isoprene and methyl acrylate to a hydroquinone catalyzed Diels-Alder reaction in the absence of a solvent, followed by dehydrogenation, hydrolysis, and oxidation. However, the Diels-Alder reaction in the aforementioned process is very slow at low temperature (7 months at 20° C.). Therefore, it is necessary to provide an additional energy source for heating so as to accelerate the reaction (6 hours at 120° C., 2 hours at 200° C., and a flow system at 400° C.). Moreover, the selectivity for a para product is lowered when the reaction temperature is raised. Additionally, as oxidation is performed in the presence of chromium (VI) trioxide (as a catalyst), heavy metal contamination will inevitably cause waste water problem. Therefore, a final mixture of the terephthalic acid and isophthalic acid obtained from the aforementioned process needs to be further separated using other reagents.

TAKASHI et al. (*J. Org. Chem.* 1966, 31(4), 1121-1123) discloses a process for producing methyl 4-methyl-3-cyclohexene-1-carboxylate by subjecting isoprene and methyl acrylate to an aluminum chloride catalyzed Diels-Alder reaction in the presence of benzene. However, the aforementioned process involves not only costs of the consumption of an organic solvent such as benzene, but also problems of solvent pollution and recovery. Moreover, although in general product yield can be increased by using a solvent in a reaction, the product yield of the aforementioned process is only 50% after a 3-hour reaction at a temperature ranging from 10° C. to 20° C.

SUMMARY OF THE INVENTION

Therefore, an object of the present invention is to provide a method for producing terephthalic acid so as to overcome the above-mentioned drawbacks, such as consumption of an organic solvent and energy.

According to one aspect of this invention, there is provided a method for producing terephthalic acid, which comprises the steps of:

subjecting methyl acrylate to contact with aluminum chloride so as to form a complex;

adding isoprene to the complex to result in a Diels-Alder reaction which is kept at a temperature no higher than 50° C. by cooling so as to obtain a cyclic adduct product;

subjecting the cyclic adduct product to separation so as to obtain a cyclic para-precursor; and subjecting the cyclic para-precursor to a chemical reaction so as to obtain terephthalic acid.

According to another aspect of this invention, there is provided a method for producing methyl 4-methyl-3-cyclohexene-1-carboxylate, which comprises the steps of:

subjecting methyl acrylate to contact with aluminum chloride so as to form a complex;

adding isoprene to the complex to result in a Diels-Alder reaction which is kept at a temperature no higher than 50° C. by cooling so as to obtain a cyclic adduct product; and subjecting the cyclic adduct product to separation so as to obtain methyl 4-methyl-3-cyclohexene-1-carboxylate.

An advantage of the method of this invention is that use of an organic solvent and thermal energy can be effectively reduced so as to alleviate damage to the environment and reduce the consumption of energy. In addition, a cyclic para-precursor (i.e., methyl 4-methyl-3-cyclohexene-1-carboxylate) for producing terephthalic acid can be produced in a high yield and with a high selectivity.

DETAILED DESCRIPTION OF THE PREFERRED EMBODIMENTS

A method for producing terephthalic acid of this invention comprises the steps of:

subjecting methyl acrylate to contact with aluminum chloride so as to form a complex;

adding isoprene to the complex to result in a Diels-Alder reaction which is kept at a temperature no higher than 50° C. by cooling so as to obtain a cyclic adduct product;

subjecting the cyclic adduct product to separation, for example, via distillation under reduced pressure, so as to obtain a cyclic para-precursor (i.e., methyl 4-metyl-3-cyclohexene-1-carboxylate); and subjecting the cyclic para-precursor to a chemical reaction so as to obtain terephthalic acid.

A lower reaction temperature can help reduce the consumption of thermal energy. In this invention, the Diels-Alder reaction is kept at a temperature no higher than 50° C. by cooling. The Diels-Alder reaction is kept at a temperature preferably ranging from −20° C. to 50° C., more preferably from −10° C. to 30° C., and most preferably from 0° C. to 5° C.

The Diels-Alder reaction in this invention is performed for a period preferably ranging from 1 hour to 24 hours, more preferably from 2 hours to 10 hours, and most preferably from 2 hours to 3 hours.

The molar ratio of aluminum chloride to isoprene ranges preferably from 0.1:1 to 0.5:1.

The chemical reaction for obtaining terephthalic acid from the cyclic para-precursor includes dehydrogenation, hydrolysis, and oxidation.

Preferably, the dehydrogenation is performed by heating in the presence of a palladium/alumina ($Pd/Al_2O_3$) catalyst.

Isoprene may be prepared from terpene-containing natural material (e.g., turpentine) or from natural rubber. Methyl acrylate may be prepared by subjecting acrylic acid to methyl esterification. Acrylic acid may be prepared by subjecting biomasses (e.g., glucose) to fermentation and dehydration.

The following examples are provided to illustrate the preferred embodiments of the invention, and should not be construed as limiting the scope of the invention.

EXAMPLES

<Example 1> E1

A. Diels-Alder Reaction

Methyl acrylate (75.8 g) and aluminum chloride (9.78 g) were homogeneously mixed in a 250 mL round-bottom flask to obtain a mixture. Isoprene (50 g) was slowly added to the mixture (a molar ratio of methyl acrylate, aluminum chloride, and isoprene was 1.2:0.1:1.0) under an ice bath with stirring at 0° C. (no solvent). After two hours, to the mixture was added water (200 mL) and ethyl acetate (200 mL). The mixture was stirred for further 10 minutes. Then the organic layer (ethyl acetate layer) was separated and washed with saturated aqueous sodium bicarbonate solution. The organic layer was then concentrated under reduced pressure to obtain a crude product. The para-position product in the crude product has a selectivity of 93.5% as analyzed by $^1$H NMR. The crude product was distilled under reduced pressure for separation, and a distillation product at a temperature ranging from 80° C. to 84° C. was collected under a pressure of 10 mmHg so as to obtain a precursor (95.2 g).

The precursor was analyzed using nuclear magnetic resonance (NMR), and the result is shown below:

$^1$H NMR (400 MHz, CDCl$_3$) δ:5.37 (br s, 1H), 3.68 (s, 3H), 2.44-2.53 (m, 1H), 2.20-2.23 (m, 2H), 1.97-2.02 (m, 3H), 1.66-1.76 (m, 1H), and 1.64 (s, 3H). According to the analysis result, the precursor is confirmed to be methyl 4-methyl-3-cyclohexene-1-carboxylate.

B. Dehydrogenation

Methyl 4-methyl-3-cyclohexene-1-carboxylate (7.68 g) obtained in step A was dissolved in triethylene glycol dimethyl ether (200 mL) at room temperature. Pd/Al$_2$O$_3$ (1.7 g, 0.5 g %) was then added. A reaction was allowed to take place by heating under reflux at 210° C. for 10 hours and was then cooled to room temperature using a water bath. The organic layer (an ether layer) was extracted using a mixture of water (200 mL) and ether (400 mL), and was then washed three times with water (300 mL) so as to remove residual triethylene glycol dimethyl ether. Water was removed using magnesium sulfate, and solvent was then removed by rotary concentration so that a dehydrogenated product (7.51 g) was obtained.

The dehydrogenated product was analyzed by $^1$H NMR and was confirmed to contain methyl 4-methylbenzoate and methyl 4-methylcyclohexanecarboxylate in a molar ratio of 85:15.

C. Hydrolysis Reaction

The dehydrogenated product (3 g) obtained in step B was dissolved in ethyl ether (50 mL). A methanol solution of sodium hydroxide (20 mL, 2 M) was then added at room temperature, followed by stirring for 20 hours. To the mixture was added water (100 mL) so as to partition the mixture and to separate a water layer from the mixture. The water layer thus obtained was then acidified with hydrochloric acid (6 M) to a pH value ranging from 2 to 3. Ethyl ether (100 mL) was then added to extract the organic product. The extracted organic product was dried with magnesium sulfate (to remove water), then concentrated in vacuo to give the hydrolysis product.

D. Oxidation

The hydrolysis product obtained in step C was dissolved in an aqueous sodium hydroxide solution (50 mL, 0.8 M), followed by cooling to 0° C. Potassium permanganate (6.32 g) was added in three aliquots at minute intervals, followed by heating to 80° C., stirring for 1 hour, and then heating to 120° C. and refluxing for 12 hours. After the reaction was cooled to room temperature, diatomaceous earth was added, followed by continuous stirring so as to adsorb residual potassium permanganate and other manganese-containing reduction products, if any. After 0.5 hour, diatomaceous earth and the materials adsorbed thereon were removed via filtration to obtain a filtrate. An aqueous sulfuric acid solution (30 mL, 18M) was added to the filtrate in an ice bath under stirring. Stirring was continued for 3 hours and, after a pH value ranging from 1 to 2 was confirmed, filtration was conducted. A solid material obtained via the filtration was dried under vacuum at 100° C. for 10 hours and was then recrystallized using dimethylacetamide (DMA) to obtain an oxidation product (i.e., terephthalic acid) crystal (1.66 g).

<Examples 2-5> E2-E5

Examples 2 to 5 were conducted in a manner similar to Example 1 except that the temperatures at which the Diels-Alder reaction was performed were −20° C., −10° C., 30° C., and 50° C., respectively.

<Example 6> E6

Example 6 was conducted in a manner similar to Example 1 except that the Diels-Alder reaction was performed for a period of 10 hours.

<Examples 7-9> E7-E9

Examples 7-9 were conducted in a manner similar to Example 1 except that the molar ratios of aluminum chloride to isoprene were 0.5:1.0, 1.0:1.0, and 2.0:1.0, respectively.

<Comparative Example 1> CE 1

Comparative Example 1 was conducted according to the disclosure of TAKASHI et al. in *J. Org. Chem.* 1966, 31(4), 1121-1123. Methyl acrylate, aluminum chloride, and isoprene (in a molar ratio of 0.303:0.032:0.307) were reacted in benzene (280 mL) at a temperature ranging from 10 to 20° C. for 3 hours.

<Comparative Example 2> CE 2

Comparative Example 2 was conducted according to the disclosure of Nazarov et al. in *Russ. Chem. Bull.* 1959, 8, 1362-1369. Methyl acrylate, hydroquinone, and isoprene (in a molar ratio of 0.3485:0.0009:0.2936) were reacted in the absence of a solvent at 120° C. for 6 hours.

<Comparative Examples 3-7> CE 3-CE 7

Comparative Examples 3-7 were conducted in a manner similar to Example 1 except that scandium (III) triflate, iron (III) chloride, copper (II) trifluoromethanesulfonate, tin (II)

chloride, and zinc trifluoromethanesulfonate were respectively used in Comparative Examples 3-7 in place of aluminum chloride, that the Diels-Alder reaction in Comparative Examples 3-7 was performed for a period of 24 hours, and that the temperature at which the Diels-Alder reaction was carried out in Comparative Examples 4 was 25° C.

The reaction conditions for the Diels-Alder reaction and the yield of the crude product and the selectivity of the para-position product in the crude product in Examples 1-9 and Comparative Examples 1-7 are shown in Table 1.

TABLE 1

|     | solvent | catalyst | Molar ratio of catalyst to isoprene | Reaction temperature (° C.) | Reaction period (hrs) | Yield | Selectivity of para product |
|-----|---------|----------|-------------------------------------|------------------------------|------------------------|-------|------------------------------|
| E1  | —       | $AlCl_3$ | 0.1:1  | 0     | 2  | 84% | 93.5% |
| E2  | —       | $AlCl_3$ | 0.1:1  | −20   | 2  | 74% | 91%   |
| E3  | —       | $AlCl_3$ | 0.1:1  | −10   | 2  | 79% | 91%   |
| E4  | —       | $AlCl_3$ | 0.1:1  | 30    | 2  | 77% | 94%   |
| E5  | —       | $AlCl_3$ | 0.1:1  | 50    | 2  | 66% | 86%   |
| E6  | —       | $AlCl_3$ | 0.1:1  | 0     | 10 | 71% | 93%   |
| E7  | —       | $AlCl_3$ | 0.5:1  | 0     | 2  | 76% | 79%   |
| E8  | —       | $AlCl_3$ | 1:1    | 0     | 2  | 73% | 76%   |
| E9  | —       | $AlCl_3$ | 2:1    | 0     | 2  | 68% | 69%   |
| CE1 | Benzene | $AlCl_3$ | 0.1:1  | 10-20 | 3  | 50% | 95%   |
| CE2 | —       | hydroquinone | 0.003:1 | 120 | 6 | 74% | 79% |
| CE3 | —       | $Sc(OTf)_3$ | 0.1:1 | 0  | 24 | 39% | N/A |
| CE4 | —       | $FeCl_3$ | 0.1:1  | 25    | 24 | 26% | N/A   |
| CE5 | —       | $Cu(OTf)_2$ | 0.1:1 | 0  | 24 | 5%  | N/A   |
| CE6 | —       | $SnCl_2$ | 0.1:1  | 0     | 24 | 0%  | N/A   |
| CE7 | —       | $Zn(OTf)_2$ | 0.1:1 | 0  | 24 | 0%  | N/A   |

N/A: not available

As shown in Table 1, in Examples 1-9, the Diels-Alder reaction was performed using aluminum chloride as a catalyst in the absence of a solvent. The yield of each of the crude products obtained in Examples 1-9 is greater than 66%, and the selectivity of each of the para products obtained in Examples 1-9 is not less than 69%. Specifically, the yield of each of the crude products obtained in Examples 1-4 and 7 is not less than 74%, and the selectivity of each of the para products obtained in Examples 1-4 is not less than 91%. In Comparative Example 1, the Diels-Alder reaction was performed in the presence of benzene, and the yield of the crude product is only 50%. In Comparative Examples 2-7, the Diels-Alder reaction was performed using other catalysts than aluminum chloride in the absence of a solvent, and the yield of each of the crude products is not greater than 74%. Specifically, in Comparative Example 2, the Diels-Alder reaction was performed at a relatively high temperature of 120° C. for a relatively long period of 6 hours to obtain the 74% yield of the crude product and the 79% selectivity of the para product. The yield of each of the crude products in Comparative Examples 5-7 is only 0-5%.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for producing terephthalic acid, comprising the steps of:
   subjecting methyl acrylate to contact with aluminum chloride so as to form a complex;
   adding isoprene to the complex to result in a Diels-Alder reaction which is kept at a temperature no higher than 50° C. by cooling so as to obtain a cyclic adduct product;
   subjecting the cyclic adduct product to separation so as to obtain a cyclic para-precursor; and
   subjecting the cyclic para-precursor to a chemical reaction so as to obtain terephthalic acid.

2. The method according to claim 1, wherein the chemical reaction includes dehydrogenation, hydrolysis, and oxidation.

3. The method according to claim 1, wherein the Diels-Alder reaction is kept at a temperature ranging from −20° C. to 50° C.

4. The method according to claim 3, wherein the temperature ranges from −10° C. to 30° C.

5. The method according to claim 4, wherein the temperature ranges from 0° C. to 5° C.

6. The method according to claim 1, wherein the Diels-Alder reaction takes place for a period ranging from 1 hour to 24 hours.

7. The method according to claim 6, wherein the period ranges from 2 hours to 10 hours.

8. The method according to claim 7, wherein the period ranges from 2 hours to 3 hours.

9. The method according to claim 1, wherein a molar ratio of aluminum chloride to isoprene ranges from 0.1:1 to 0.5:1.

10. The method according to claim 2, wherein the dehydrogenation is performed by heating in the presence of a palladium/alumina catalyst.

11. The method according to claim 1, wherein the cyclic para-precursor comprises methyl 4-methyl-3-cyclohexene-1-carboxylate.

12. A method for producing methyl 4-methyl-3-cyclohexene-1-carboxylate, comprising the steps of:
   subjecting methyl acrylate to contact with aluminum chloride so as to form a complex;
   adding isoprene to the complex to result in a Diels-Alder reaction which is kept at a temperature no higher than 50° C. by cooling so as to obtain a cyclic adduct product; and
   subjecting the cyclic adduct product to separation so as to obtain methyl 4-methyl-3-cyclohexene-1-carboxylate.

* * * * *